US008828739B2

(12) United States Patent
Guo et al.

(10) Patent No.: US 8,828,739 B2
(45) Date of Patent: *Sep. 9, 2014

(54) LATERAL FLOW IMMUNOASSAY CONTROLS

(75) Inventors: Huiyan Guo, San Diego, CA (US); Min Wang, San Diego, CA (US); Tao Shang, Hangzhou (CN); Hui-Kang Chen, Hangzhou (CN); Fei Gao, Hangzhou (CN)

(73) Assignee: Alere Switzerland GmbH, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/481,599

(22) Filed: May 25, 2012

(65) Prior Publication Data

US 2012/0237923 A1    Sep. 20, 2012

Related U.S. Application Data

(60) Division of application No. 12/262,079, filed on Oct. 30, 2008, now Pat. No. 8,193,002, which is a continuation of application No. 10/775,274, filed on Feb. 10, 2004, now Pat. No. 7,459,314.

(60) Provisional application No. 60/447,376, filed on Feb. 13, 2003.

(51) Int. Cl.
*G01N 33/53* (2006.01)
*G01N 33/52* (2006.01)

(52) U.S. Cl.
CPC .................. *G01N 33/521* (2013.01)
USPC ........... 436/514; 422/400; 422/420; 422/421; 422/425; 436/518; 436/164; 436/169; 435/283.1; 435/287.1; 435/287.9

(58) Field of Classification Search
CPC ......... C12M 1/34; G01N 33/53; G01N 33/58; G01N 2021/75; G01N 2021/752; G01N 2021/757; G01N 2021/77; G01N 2021/7759; G01N 2035/00108; B01N 2300/0825; C12Q 1/04; B01L 2400/0406
See application file for complete search history.

(56) References Cited

U.S. PATENT DOCUMENTS

| 4,275,149 A | 6/1981 | Litman |
| 4,299,916 A | 11/1981 | Litman |
| 4,703,017 A | 10/1987 | Campbell |
| 4,857,453 A | 8/1989 | Ullman |

(Continued)

FOREIGN PATENT DOCUMENTS

WO    WO 88/08534    11/1988

OTHER PUBLICATIONS

U.S. Appl. No. 09/579,673, filed May 26, 2003, Hudak.

*Primary Examiner* — Melanie Y Brown
*Assistant Examiner* — Rebecca Martinez
(74) *Attorney, Agent, or Firm* — DLA Piper LLP (US)

(57) ABSTRACT

Rapid lateral flow immunoassays have an extensive history of use in both the clinical and home settings. These devices are used to test for a variety of analytes, such as drugs of abuse, hormones, proteins, urine or plasma components and the like. The present invention provides an improved procedural control that indicates to the test user that at least a portion of the applied sample has passed through the test result zone of the test strip, and optionally that the test is complete and the test results may be read.

8 Claims, 4 Drawing Sheets

(56) References Cited

U.S. PATENT DOCUMENTS

| | | |
|---|---|---|
| 4,943,522 A | 7/1990 | Eisinger |
| 5,119,830 A | 6/1992 | Davis |
| 5,591,645 A | 1/1997 | Rosenstein |
| 5,602,040 A | 2/1997 | May |
| 5,622,871 A | 4/1997 | May |
| 5,656,503 A | 8/1997 | May |
| 5,714,389 A | 2/1998 | Charlton |
| 5,770,460 A | 6/1998 | Pawlak |
| 5,776,713 A | 7/1998 | Garner |
| 5,916,815 A | 6/1999 | Lappe |
| 5,989,921 A | 11/1999 | Charlton |
| D430,303 S | 8/2000 | Cipkowski |
| 6,187,598 B1 | 2/2001 | May |
| 6,248,592 B1 | 6/2001 | Nogar |
| 6,352,862 B1 | 3/2002 | Davis |
| 6,372,514 B1 | 4/2002 | Lee |
| 6,372,516 B1 | 4/2002 | Sun |
| 6,403,383 B1 | 6/2002 | Casterlin |
| 6,406,922 B2 | 6/2002 | Casterlin |
| 6,485,982 B1 | 11/2002 | Charlton |
| 6,565,808 B2 | 5/2003 | Hudak |
| 6,617,123 B1 | 9/2003 | Smith |
| 6,627,459 B1 | 9/2003 | Tung |
| 6,855,561 B2 * | 2/2005 | Jerome et al. .................. 436/514 |
| 6,890,484 B2 | 5/2005 | Bautista |
| 7,226,793 B2 | 6/2007 | Jerome |
| 7,459,314 B2 * | 12/2008 | Guo et al. ...................... 436/514 |
| 2003/0049167 A1 * | 3/2003 | Jerome et al. ................... 422/58 |
| 2004/0184954 A1 | 9/2004 | Guo |

\* cited by examiner

Before Sample

After Sample

LATERAL FLOW IMMUNOASSAY CONTROLS

CROSS-REFERENCE TO RELATED APPLICATIONS

This application is a divisional application of U.S. application Ser. No. 12/262,079 filed Oct. 30, 2008, now U.S. Pat. No. 8,193,002; which is a continuation application of U.S. application Ser. No. 10/775,274 filed Feb. 10, 2004, now issued as U.S. Pat. No. 7,459,314; which claims the benefit under 35 USC §119(e) to U.S. Application Ser. No. 60/447,376 filed Feb. 13, 2003. The disclosure of each of the prior applications is considered part of and is incorporated by reference in the disclosure of this application.

BACKGROUND OF THE INVENTION

1. Field of the Invention

The present invention relates generally to the fields of immunoassay and chemical test devices that can be used to test for the presence of an analyte. In particular, the present invention relates to new procedural controls.

2. Background Information

Rapid lateral flow immunoassays and chemical test devices have an extensive history of use in both the clinical and the home settings. These devices are used to test for a variety of analytes, such as drugs of abuse, hormones, proteins, urine or plasma components and the like. The home pregnancy test, which requires a woman to urinate on a wick protruding from the test device and tells her if she is pregnant in a few minutes, is one such device with which many people are familiar.

These devices generally comprise a lateral flow test strip, such as nitrocellulose or filter paper, a sample application area, test results area and an analyte specific binding reagent that is bound to some kind of detectable label, such as a colored particle or an enzyme detection system. U.S. Pat. No. 6,485,982, U.S. Pat. No. 6,187,598, U.S. Pat. No. 5,770,460, U.S. Pat. No. 5,622,871, co-owned U.S. Pat. No. 6,565,808, and co-pending patent applications U.S. Ser. No. 10/278,676, U.S. Ser. No. 09/579,673 and U.S. Ser. No. 10/717,082, which are incorporated herein by reference, are non-limiting examples of such lateral flow test devices.

The present invention provides an improved procedural control, which indicates to the user that at least a portion of an applied sample solution has passed through the portion of the test strip upstream from the control zone, especially the test result zone, and optionally that the test is complete. At the completion of the test, the user may read the test results.

SUMMARY OF THE INVENTION

As a non-limiting introduction to the breath of the present invention, the present invention includes several general and useful aspects, including:

1. An improved procedural control, for lateral flow test devices, which indicates to the user that at least a portion of an applied sample has passed through the test result zone of the test strip, and optionally that the test is completed.
2. An analytical test device for detecting an analyte suspected of being present in a liquid sample, the device comprising: a test strip, wherein said test strip further comprises a sample application zone, a test result zone, a control result zone and optionally a reagent zone; an analyte detection means; and a control detection means.
3. An improved procedural control for lateral flow analytical test devices for detecting an analyte suspected of being present in a sample, the improved procedural control comprising: a test strip; a control zone; and a control detection means.
4. An analytical lateral flow test device for detecting an analyte suspected of being present in a liquid sample having a test strip, and analyte detection means, a test result zone and a control means, the control means comprising: a first dye indicator having a first color and a second dye indicator having a second color, said first and second dye indicators being applied to the same application location on the test strip and said applied first and second dye indicators appearing to the user as a color other than the color of said second dye indicator.

These aspects of the invention, as well as others described herein, can be achieved by using the methods, articles of manufacture and compositions of mater described herein. To gain a full appreciation of the scope of the present invention, it will be further recognized that various aspects of the present invention can be combined to make desirable embodiments of the invention.

DETAILED DESCRIPTION OF THE INVENTION

Definitions

Figure 1A:
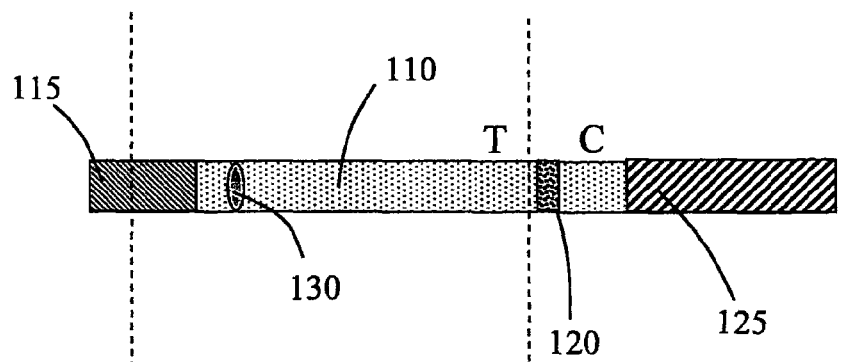
FIG. 1A is a top view of one embodiment of the present invention. The dashed arrow indicates direction of sample flow, from upstream to downstream, after the sample has been applied. The T and C indicate the test result and control zones, respectively. The test result zone T encompasses the portion of the test strip where the test results may be read by the user. The control zone C is the area of the test strip where the control results are read. Optionally the control zone C may encompass the area upstream from where the control results are read; where the control reagent 135 is applied but it is not visible to the user, depending upon the particular design of the present invention being used.

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down" or "upper" or "lower" and the like refer to orientation of the parts during use of the device. Where a term is provided in the singular, the inventors also contemplate the plutal of that term. The nomenclature used herein and the laboratory procedures described below are those well known and commonly employed in the art. As employed throughout the disclosure, the following terms, unless other wise indicated, shall be understood to have the following meanings:

A "dye" refers to a substance, compound or particle that can be detected, particularly by visual, fluorescent or instrumental means. A dye may be, for example, but not limited to, a pigment produced as a coloring agent or ink, such as Brilliant Blue, 3132 Fast Red 2R and 4230 Malachite Blue Lake, all available from Hangzhou Hongyan Pigment Chemical Company, China. The "dye" may also be a particulate label, such as, but not limited to, blue latex beads or gold particles. The particulate labels may or may not be bound to a protein, depending upon if it is desired for the particles to move in the test strip or not. If the particles are to be immobilized in the test strip, the particles may be conjugated to a protein, which in turn in bound to the test strip by either physical or chemical means.

"Mobilizable dye" refers to any detectable compound, such as the dye described supra, that can be striped or sprayed on the test strip, dried, and then dissolved by an applied liquid sample moving by capillary flow through the test strip. The dissolved mobilizable dye moves with the sample through the test strip, away from its point of application to the test strip. In a general way, mobilizable is used to indicate that an applied compound is capable of significant movement within or on the test strip, with the applied liquid sample.

"Non-mobilizable dye" in this application refers to any detectable compound that will not move substantially from its location of application, after the test strip has been dried or optionally treated to immobilize the non-mobilizable dye. The term "non-mobilizable" denotes a dye that is not dissolvable by or movable with an applied liquid sample.

In some instances, the compound chosen as an immobilized dye is only soluble in organic solvents, such as ethanol, benzene or acetone. Since the applied sample is aqueous, the dye soluble in organic liquids will not move with the aqueous sample passing through that portion of the test strip.

In other cases, a mobilizable dye is rendered non-mobilizable by linking or conjugating it to another molecule that is itself not mobilizable, such as a protein. For example, the protein to which the dye is conjugated may be immobilized onto the test strip, due to its own ability to bind the test strip material, such as untreated nitrocellulose, or it is treated to immobilize it to the test strip, such as by baking or chemical means. Since the mobilizable protein-bound dye becomes "non-mobilizable" when it is immobilized on the test strip, the dye in this situation is referred to as "non-mobilizable" as a mater of convenience.

"Analyte" is the compound or composition to be measured that is capable of binding specifically to a ligand, receptor, or enzyme, usually an antibody or antigen, such as a protein, drug, metabolite or nucleic acid. The precise nature of antigenic and druganalytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference. Analytes can include antibodies and receptors, including active fragments or fragments thereof. An analyte can include an analyte analogue, which is a derivative of an analyte, such as, for example, an analyte altered by chemical or biological methods, such as by the action of reactive chemicals, such as adulterants or enzymatic activity. An analyte can include epitopes or epitope analytes, which are epitopes altered in ways such as analytes can be altered.

A number of proteins found in human plasma are important clinically and include: prealbumin, albumin, alpha (one)-lipoprotein, alpha (one)-acid glycoprotein, alpha (one)-antitrypsin, alpha (one-glycoprotein, transcortin, 4.6S-postalbumin, tryptophan-poor alpha (one)-glycoprotein, alpha (one) chi-glycoprotein, thyroxin-binding globulin, inter-alpha-trypsin-inhibitor, Gc-globulin, haptogiobulin, ceruloplasmin, cholinesterase, alpha (two)-lipoprotein(s), myoglobin, C-reactive Protein, alpha (two)-macroglobulin, alpha (two) HS-glycoprotein, Zn-alpha two-glycoprotein, alpha (two)-neuramino-glycoprotein, erythropoietin, beta-lipoprotein, transferrin, hemopexin, fibrinogen, plasminogen, beta (two)-glycoprotein I, and beta (two)-glycoprotein II.

Specific binding proteins such as antibodies to microbial antigens, autoimmune antibodies, T cell receptors, antibodies to allergens, particularly IgE, and the like are exemplary of analytes. Complement factors and blood clotting factors are also exemplary of analytes.

Protein hormones such as Parathyroid hormone, Thyrocalcitonin, Insulin, Glucagon, Relaxin, Erythropoietin, Melanotropin, Somatotropin, Corticotropin, Thyrotropin, Follicle-stimulating hormone, Luteinizing hormone (LH), Luteomammotropic hormone, Gonadotropin (such as chorionic gonadotropin, including human chorionic gonadotropin or hCG) are important analytes, as are oxytocin, vasopressin, releasing factors (RF) CRF, LRF, TRF, somatotropin-RF, GRF, FSH-RF, PIF, and MIF. Tissue Hormones such as secretin, gastrin, angiotensin I and II, bradykinin, human placental lactogen are also exemplary of analytes.

Analytes of particular interest include drugs, metabolites, pesticides, pollutants, antibodies and the like. Included among drugs of interest are the alkaloids. Among the alkaloids are morphine alkaloids, which includes morphine, codeine, heroin, dextromethorphan their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

Another group of drugs includes steroids, which includes the estrogens, androgens, andreocortical steroids, bile acids, cardiotonic glycosides and aglycones, which include digoxin and digoxigenin, saponins and sapogenins, their derivatives and metabolites. Also included are the steroid mimetic substances, such as diethylstilbestrol.

Another group of drugs is lactams having from 5 to 6 annular or ring members, which include the barbiturates, for example phenobarbital and secobarbital, diphenylhydantonin, primidone, ethosuximide, and their metabolites. The next group of drugs is aminoalkylbenzenes, with alkyl of from 2 to 3 carbon atoms, which includes the amphetamines, catecholamines, which includes ephedrine, L-dopa, epinephrine, narcine, papaverine, and their metabolites. A further group of drugs is benzheterocyclics which include oxazepam, chlorpromazine, tegretol, imipramine, their derivatives and metabolites, the heterocyclic rings being azepines, diazepines and phenothiazines. Purine drugs include theophylline, caffeine, their metabolites and derivatives. Another group of drugs includes those derived from marijuana, which includes cannabinol and tetrahydrocannabinol.

The next group of drugs is miscellaneous individual drugs which include methadone, meprobamate, serotonin, meperidine, amitriptyline, nortriptyline, lidocaine, procainamide, acetylprocaineamide, propranolol, griseofulvin, valproic acid, butyrophenones, antihistamines, anticholinergic drugs, such as atropine, their metabolites and derivatives.

Another group of drugs is antibiotics, which include penicillin, chloromycetin, actinomycetin, tetracycline, terramycin, the metabolites and derivatives. The next group of drugs is aminoglycosides, such as gentamicin, kanamicin, tobramycin, and amikacin.

Metabolites related to metabolic states or disease states that can be analytes include glucose, spermine, galactose, phenylpyruvic acid, and porphyrin Type 1. Also included are the nucleosides and nucleotides, which include ATP, AND, FMN, adenosine, guanosine, thymidine, and cytidine with their appropriate sugar and phosphate substituents. Other compounds that can be analytes include the vitamins such as A, B, for example, B12, C, D, E and K, folic acid, and thiamine. Prostaglandins, which differ by the degree and sites of hydroxy lation and unsaturation, can also be analytes.

Among pesticides of interest are polyhalogenated biphenyls, phosphate esters, thiophosphates, carbamates, polyhalogenated sulfenamides, their metabolites and derivatives. Exemplary of microbiological analytes are lipsopolysaccharides, proteins and nucleic acids from organisms such as chlamydia, herpes virus, hepatitis virus (A, B, or non-A-non-B), HIV, gonorrhea, *H. pilori, T. pallidum*, and the like.

An analyte can also be an analyte relating to measuring or determining the adulteration of a sample, such as by diluting a sample, providing a sample from another species, subject or non-human source, or adding an agent that can alter the composition of a sample. Such adulteration analytes can be chosen based on the subject, the sample type being analyzed and the source or type of expected adulteration. Such analytes are optionally referred to herein as adulteration analytes or adulteration indicators.

"Antibody" is an immunoglobulin, or derivative or fragment or active fragment thereof, having an area on the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

A "test strip" can include one or more bibulous or non-bibulous materials. If a test strip comprises more than one material, the one or more materials are preferably in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another. Suitable materials for test strips include, but are not limited to, materials derived from cellulose, such as filter paper, chromatographic paper, nitrocellulose, and cellulose acetate, as well as materials made of glass fibers, nylon, dacron, PVC, polyacrylamide, cross-linked dextran, agarose, polyacrylate, ceramic materials, and the like. The material or materials of the test strip may optionally be treated to modify their capillary flow characteristics or the characteristics of the applied sample. For example, the sample application region of the test strip may be treated with buffers to correct the pH or specific gravity of an applied urine sample, to ensure optimal test conditions.

The material or materials can be a single structure such as a sheet cut into strips or it can be several strips or particulate material bound to a support or solid surface such as found, for example, in thin-layer chromatography and may have an absorbent pad either as an integral part or in liquid contact. The material can also be a sheet having lanes thereon, capable of spotting to induce lane formation, wherein a separate assay can be conducted in each lane. The material can have a rectangular, circular, oval, triagonal or other shape provided that there is at least one direction of traversal of a test solution by capillary migration. Other directions of traversal may occur such as in an oval or circular piece contacted in the center with the test solution. However, the main consideration is that there be at least one direction of flow to a predetermined site. In the following discussion strips will be described by way of illustration and not limitation.

The support for the test strip, where a support is desired or necessary, will normally be water insoluble, frequently non-porous and rigid but may be elastic, usually hydrophobic, and porous and usually will be of the same length and width as the strip but may be larger or smaller. The support material can be transparent, and, when a test device of the present invention is assembled, a transparent support material can be on the side of the test strip that can be viewed by the user, such that the transparent support material forms a protective layer over the test strip where it may be exposed to the external environment, such as by an aperture in the front of a test device. A wide variety of non-mobilizable and non-mobilizable materials, both natural and synthetic, and combinations thereof, may be employed provided only that the support does not interfere with the capillary action of the material or materials, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like. Elastic supports may be made of polyurethane, neoprene, latex, silicone rubber and the like.

A "control zone" is a region of a test strip in which a dye as described supra can be observed to shift location, appear, change color, or optionally to disappear. Detection or observation of the control zone may be done by any convenient means, depending upon the particular choice of dye, especially, for example but not limited to, visually, fluorescently, by reflectance, radiographically, and the like. As will be described, the dye may or may not be applied directly to the control zone, depending upon the design of the control being used.

A "label" may be any molecule bound to a specific binding member that can produce a detectable signal. In the present invention, the label may be inert and provide a signal by concentrating in the detection zone, or it may serve solely as a binding site for a member of the signal producing system, or it may spontaneously produce a detectable signal or may produce a detectable signal in conjunction with a signal producing system. The label may be isotopic or nonisotopic.

"Proximal end" refers to the end of a test device or test strip that includes the sample application aperture of the test device and sample application zone of the test strip.

"Reagent zone" refers to a region of a test strip where reagent is provided. The reagent zone can be on a reagent pad, a separate segment of bibulous or non-bibulous material included on the test strip, or it can be a region of a bibulous or non-bibulous material of a test strip that also includes other zones, such as an analyte detection zone. The reagent zone can carry a detectable label, which may be a direct or indirect label. Preferably the reagent is provided in a form that is immobile in the dry state and mobile in the moist state. A reagent can be a specific binding member, an analyte or analyte analog, an enzyme, a substrate, indicators, components of a signal producing system, chemicals or compounds such as buffering agents, reducing agents, chelators, surfactants, etc., that contribute to the function of the test strip assay.

"Sample" is any material to be tested for the presence or amount of an analyte. Preferably, a sample is a fluid sample, preferably a liquid sample. Examples of liquid samples that may be tested using a test device of the present invention include bodily fluids including blood, serum, plasma, saliva, urine, ocular fluid, semen, and spinal fluid; water samples, such as samples of water from oceans, seas, lakes, rivers, and the like, Or samples from home, municipal, or industrial water sources, runoff water or sewage samples; and food samples, such as milk or wine. Viscous liquid, semi-solid, or solid specimens may be used to create liquid solutions, eluates, suspensions, or extracts that can be samples. For example, throat or genital swabs may be suspended in a liquid solution to make a sample.

"Sample application aperture" refers to the portion of a test device where an opening in the test device provides access to the sample application zone of the test strip. In one embodiment of the present invention, a sample application aperture is created by an open-ended channel at the proximal end of the test device. Preferably, a test strip in engaged in the open-ended channel such that sample contacted with the sample application aperture is thereby applied to the test strip. In an alternate embodiment, a sample application aperture is formed by an opening in the front of a test device, such that the sample application zone of the test strip is in fluid communication with the exterior of the test device.

"Sample application zone" is the portion of a test strip where sample can be applied. The sample application zone of a test strip of the present invention preferably occurs at the sample application aperture of a test device of the present invention, and is in fluid communication with the sample application aperture.

"Specific binding member" is one of two different molecules having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormone-hormone receptor, nucleic acid duplexes, IgG-protein A, DNA-DNA, DNA-RNA, and the like are not immunological pairs but are included in the definition. In the case of binding pairs such as avidin-biotin, reagent can be labeled with one member of this pair and a detection zone can include the other member of this pair in a capture type assay. Other general types of assays using avidin-biotin pairs or binding pairs of this type are known in the art. In addition, an antigen or epitope can be labeled for use as a reagent for the detection of antibodies that bind with or specifically bind with such an antigen or epitope. In one aspect of this type of assay, an antigen or epitope can be detectably labeled and present in the reagent zone and the antigen or epitope can be present in a detection zone. This type of assay can be used, for example, to detect antibodies such as antibodies that bind with or specifically bind with an etiological agent in a sample. Other general types of assays using labeled antigen or labeled epitopes are known in the art.

"Test results zone" is a region of a test strip that provides a detectable signal indicating the presence of the analyte. The test results zone can include an immobilized binding reagent specific for an analyte ("specific binding member"), and/or an enzyme that reacts with the analyte. A test results determination zone can include one or more analyte detection zones. Other substances that may allow or enhance detection of the analyte, such as substrates, buffers, salts, may also be provided in the test results determination zone. One or more members of a signal producing system may be bound directly or indirectly to the detection zone. A test results determination zone can optionally include one or more control zones that provide indication that the test has been performed properly.

Other technical terms used herein have their ordinary meaning in the art that they are used, as exemplified by a variety of technical dictionaries.

Improved Lateral Flow Immunoassay Controls

Figure 1B:
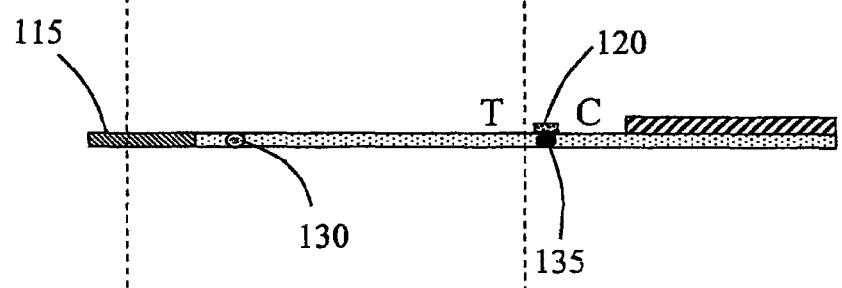
FIG. 1B is a side view of the embodiment illustrated in FIG. 1A, prior to the addition of the sample 145. The cartoon illustrates the location of the labeled specific reagent 130 and at least one control dye 135. In this cartoon, only one control dye 135 is pictured and the control dye 135 is screened from the view of the user by a visible barrier 120.
Figure 1C:
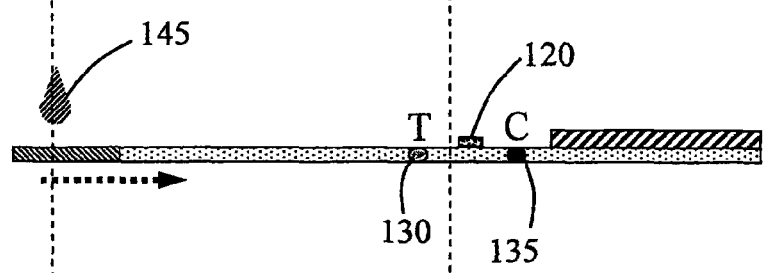
FIG. 1C is a side view of the embodiment illustrated in FIG. 1A, showing the location of the labeled specific reagent 130 and the control dye 135 after the sample 145 has been added. Note that the labeled specific reagent 130 and the control dye 135 have moved downstream from their location shown in FIGS. 1A and 1B. To the user, it would look like a line or smear of dye had appeared or moved into the control zone, indicated by C.

Turning now to the figures, FIGS. 1A, 1B and 1C illustrate, by way of example, a top view of a lateral flow test strip having the improved control of the present invention, comprising a sample application area 115, test result zone "T," a control zone "C," and an absorbent body 125 is shown in FIG. 1A. The sample application area 115 may optionally include a sample application pad, made of a material different from the material of the test strip.

Certain embodiments of the improvement of the present invention comprise a dye 135 applied to the test strip 110 downstream from the test result zone "T". In FIG. 1A, the control dye 135 is not visible, because the dye 135 is covered by a physical barrier 120, which shields the dye 135 from the user's view prior to sample application. The physical barrier 120 may be constructed of any convenient liquid-impermeable material, such as plastic coated paper, tape, plastic, metal foil or paint.

Looking at FIG. 1B, a side view of the embodiment of the present invention shown in FIG. 1A, one can observe that the control dye 135 is applied to the test strip 110 upstream from the test result zone "T." The control dye 135 is screened from the user's view, prior to sample application by the physical barrier 120. One aspect of the present invention is a dye 135 is mobilizable, as discussed in definitions supra. Generally, any convenient mobilizable dye can be used, as long as it can be detected. A variety of colored mobilizable dyes have been found to work, such as, for example, Ponceau 4R and green coloring matter from the Shanghai Dye Institute, Rose Red lot 020811 from Shanghai Marine Painting Materials Company, watercolor pigments and commonly available food colorings.

During the manufacture of the test strip, the control dye 135 is striped or sprayed on the test strip 110 and generally is absorbed into the test strip 110 so that the control dye 135 is not sitting on the surface of the test strip 110. The physical barrier 120 is then applied to the test strip 110 and screens the control dye 135 from the view of the user prior to application of a sample 145.

FIGS. 1A and 1B also show that a detectable labeled analyte-specific binding reagent 130 is located near, or optionally at, the sample application area 115.

When the sample 145 is applied to the sample application area 115 (see FIG. 1C), the sample 145 is absorbed by the sample application area 115 and begins to move downstream in the test strip 110 by capillary action (dashed arrow). When the sample 145 reaches the labeled specific binding reagent 130, the labeled specific binding reagent 130 is dissolved by the liquid sample 145 and becomes dispersed within the sample 145. The specific binding reagent 130 begins to bind to analyte present in the applied sample 145. The sample 145 continues traveling downstream, carrying populations of unbound analyte, unbound specific binding reagent 130 and analyte bound by labeled specific binding reagent 130.

As the sample migrates downstream, it reaches a band of unlabeled analyte specific binding reagent immobilized in the test result zone "T" (not shown). The unlabeled specific binding reagent captures the analyte present in the sample 145. If the analyte is present in the sample, analyte binding by the immobilized, unlabeled specific binging reagent causes a build-up of the label, and the appearance of a detectable line at "T." For example, if the label is blue latex particles, a blue line will appear at the "T". Labeled specific binding reagent 130 that is not bound to analyte will continue to flow downstream' of the "T" with the rest of sample. The labeled specific binding reagent 130 unbound to analyte will not be caught by the immobilized unlabeled specific binding reagent.

FIG. 1C illustrates what the test strip might look like a few minutes after the sample has been applied. In FIG. 1C, one sees that the control dye 135 will be dissolved by the liquid sample 145 and carried to the control zone (denoted by "C"). Depending upon how the device is constructed, the control dye 135 in the control zone "C" will appear as a band or a smear filling the "C" area with color of fluorescence. For example, if the dye is Ponceau 4B, a red smear will appear at the "C". The appearance of the control dye 135 indicates that at least a portion of the applied sample has passed through the test result zone. Optionally, the appearance of the control dye 135 may indicate that the test is complete and the test results may now be read.

Figure 1D:
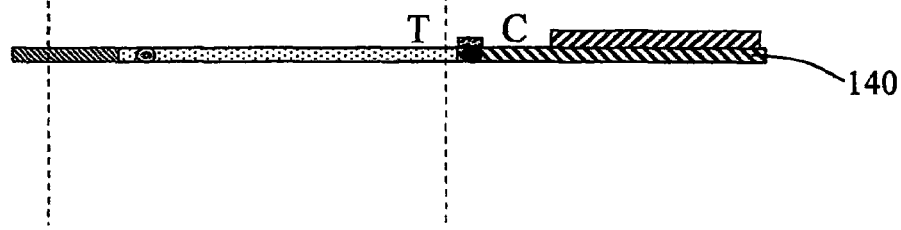
FIG. 1D is a side view of another aspect of the present invention shown in FIG. 1A. Notice that the portion of the test strip down stream from the test zone T has been replaced with a material different from the rest of the test strip 110. For example, the upstream portion of the test strip 110 could comprise nitrocellulose. The downstream portion of the test strip 140 could be absorbent filter paper.

In certain embodiments of the present invention (see FIG. 1D), the downstream portion of the test strip 110 may be replaced by a material 140 different from that of the test strip 110. For example, if the test strip 110 is nitrocellulose, the portion of the test strip 110 from the barrier 120 to the extreme downstream end can be replaced with filter paper 140. In this example, the control dye 135 is sprayed or striped on the upstream end of the filter paper 140 and covered by the barrier 120. As in the previous embodiment described, the sample would dissolve the control dye 135, and carry it downstream in the filter paper 140. The control dye 135 would become visible in the control zone "C".

Figure 2A:
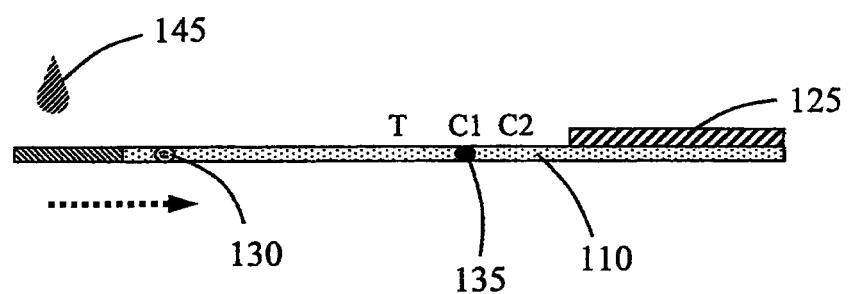
FIG. 2A is a side view of another embodiment of the present invention before application of the sample 145. Prior to application of a sample solution 145, the control dye 135 appears as a colored line at C1. This is analogous to the embodiment illustrated in FIG. 1A. However, the embodiment shown in FIG. 2A lacks a visible barrier 120 obscuring the dye 135 from the view of the user.
Figure 2B:
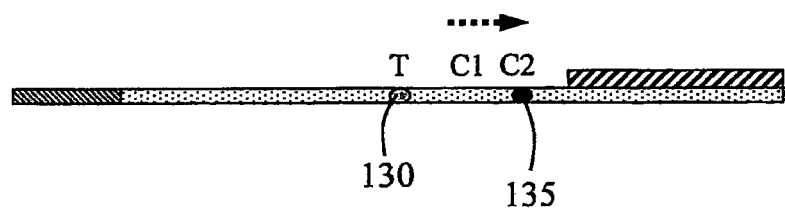
FIG. 2B is a side view of the device of FIG. 2A after the sample solution 145 has been applied to the test strip and the test is concluded. Note that the control dye 135 appears as a colored line that has moved from C1, as shown in FIG. 2A, to a position at C2. To the user, it would appear that the dye has moved from one location on the test strip (C1) to another location (C2).

In certain embodiments of the present invention, there may be no visible barrier 120 (see FIGS. 2A and 2B). Instead, the control dye 135 may be observed to move from one point to another on the test strip. For example, before the sample is applied, the control dye 125 appears as a discrete line at "C1," as shown in FIG. 2A. At the conclusion of the test, the control dye 135 has moved to "C2," where it appears as a diffused line or a smear of color (see FIG. 2B). In this embodiment of the present invention, the movement of the control dye 135 from "C1" to "C2" indicates to the user that at least a portion of the applied sample 145 has through the test result zone "T". Optionally, this movement of the control dye 135 from "C1" to "C2" indicates that the assay is complete and that the test results may be read.

Figure 3A:
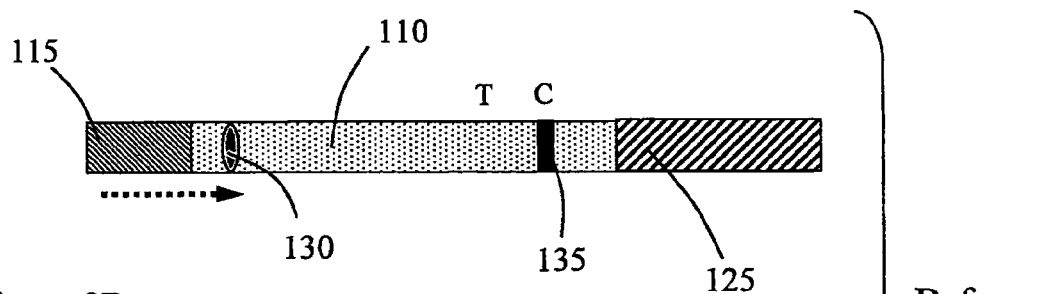
FIG. 3A is a top view of still another embodiment of the present invention, prior to addition of the sample 155. T and C indicate the test result and control zones, respectively. Notice that the control line appears to be the color of dye 310.
Figure 3B:
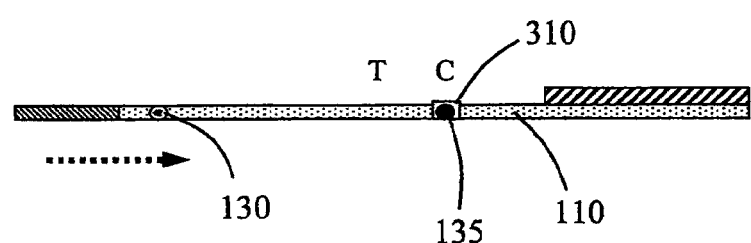
FIG. 3B is side view of the device of FIG. 3A, prior to addition of the sample 155. Notice that the control line contains two different dyes, a first dye 310 and a second dye 135. The first dye 310 is able to block out the color of the second dye 135, making the control line appear to be the color of the first dye 310.
Figure 3C:
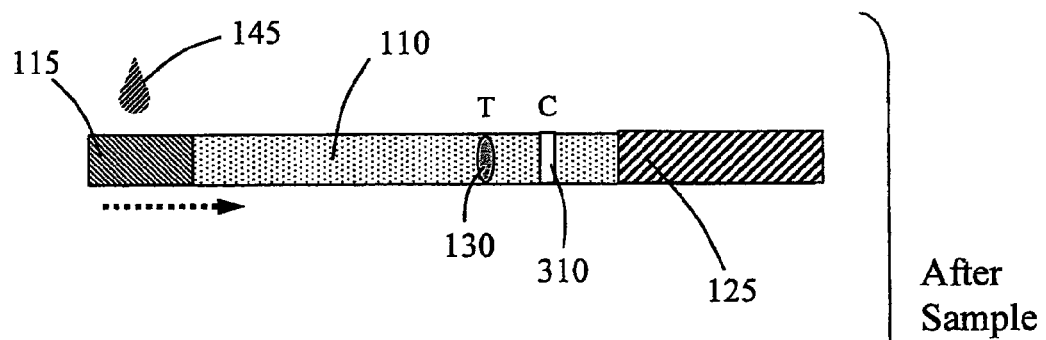
FIG. 3C is a top view of the device of FIG. 3A, after addition of the sample 155. Notice that the color of the control line appears as the color of the second dye 135.

In yet another embodiment of the present invention, two control dyes may be used (see FIGS. 3A, 3B and 3C). FIGS. 3A and 3B are top and side views illustrating the location of the two dyes before a sample 145 has been applied. Two dyes have been striped at "C", a mobilizable dye 135 (soluble in the applied sample) and an non-mobilizable dye 310 (not soluble in the applied sample). Examples of non-mobilizable dye include, but are not limited to, 3132 fast red 2R, 4230 Malachite blue lake, blue colored latex beads conjugated with BSA, and gold labeled IgG.

The mobilizable dye 135 and non-mobilizable dye 310 should have different colors and the mobilizable dye should prevent the non-mobilizable dye from detection (i.e., cover up the non-mobilizable dye). In FIGS. 3A and 3B, for example, the mobilizable dye could be red and the non-mobilizable dye could be blue. But the line "C" would appear as red or dark purple to the user. Alternatively, the colors of the two dyes may mix to produce a third color. For example, a red dye and a blue dye might initially appear like a purple line. If the blue dye is mobilizable, the line would appear red when the test was completed. In another example, two fluorescent dyes of different wavelengths might be mixed. When the sample was applied and the test allowed to run, the mobilizable fluorescent dye would move downstream from the control zone. The remaining non-mobilizable fluorescent dye would then be unobscured and detectable at its wavelength.

Figure 3D:
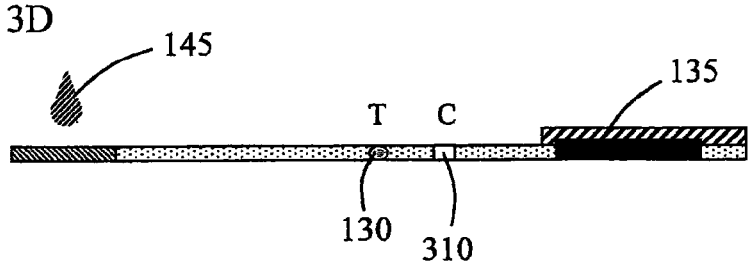
FIG. 3D is a side view of the device shown in FIG. 3C. This perspective illustrates that the first dye 310 has moved down stream, leaving the second dye 135 visible.

FIGS. 3C and 3D illustrate what happens when an applied sample 145 reaches the dyes at "C". The mobilizable dye 135 is dissolved by the sample 145 and flows downstream with the sample 145. The removal of the mobilizable dye 135 by the sample 145 uncovers the non-mobilizable dye 310. The now visible non-mobilizable dye 310 appears as a blue line where the red line previously appeared. In other words, it appears to the user that the control line "C" changed from a red or purple line to a blue line. This apparent change in color of the control line "C" indicates that at least a portion of the applied sample 145 has passed through the test result zone "T". Optionally, the apparent color change of the control line "C" indicates that the test is complete and the test results may be viewed.

Figure 4A:
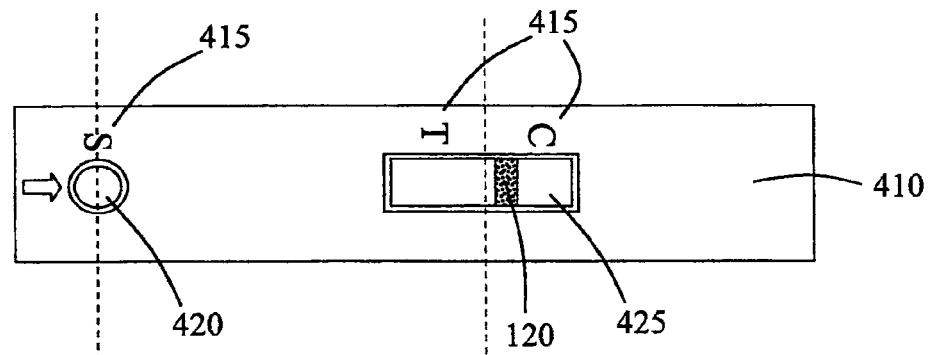
FIG. 4A is a cartoon of the top view of the device of FIG. 1A, in a casing 410, illustrating what the device and the test results might look like to a user of the device.
Figure 4B:
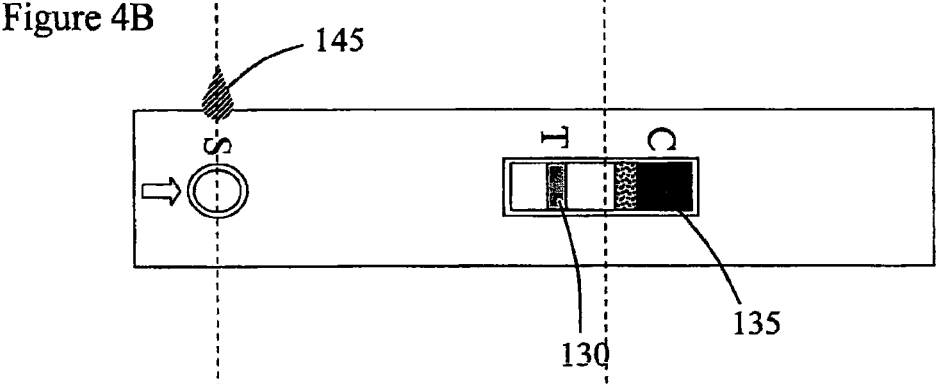
FIG. 4B is a top view of the device of FIG. 4A, after the sample has been added, illustrating how positive test results would appear to the user.
Figure 4C:
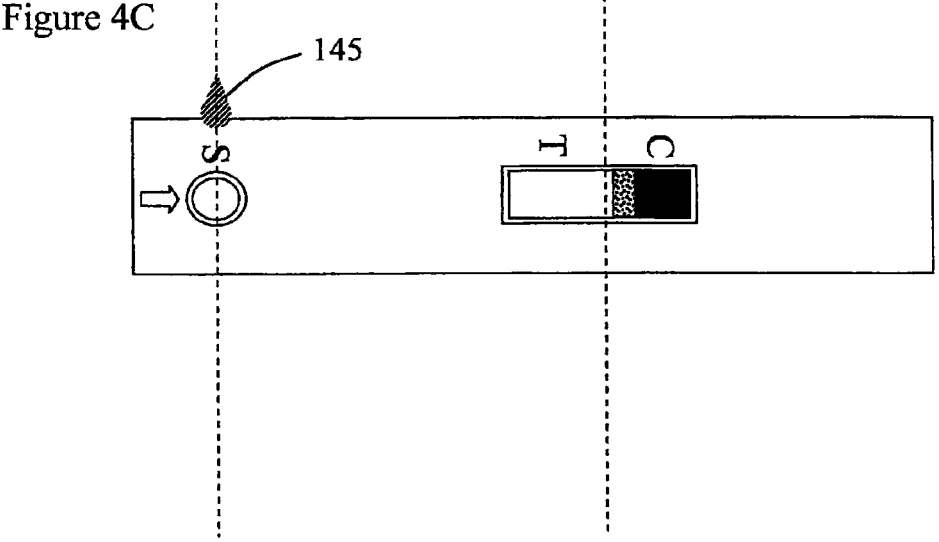
FIG. 4C is top view of the device of FIG. 4A, after the sample has been added, illustrating how negative test results would appear to the user.

FIGS. 4A, 4B and 4C are cartoons showing another embodiment of the present invention. FIG. 4A shows a test strip of the present invention, similar to that shown in FIGS. 1A, 1B and 1C, with the exception that the test strip is housed within a case 410. The case 410 screens most of the test strip from view. The case 410 comprises a sample application aperture 420, in fluid communication with the sample application area 115. The sample 145 may be applied to the sample application area 145 of the test strip through the sample application aperture 420 of the case. In FIG. 1A, no sample has been applied, so there is no color or line visible in the test and control results zones.

In additional aspects of the present invention, the case 410 comprises at least one results observation window 425. FIG. 4A shows one large window, in which the test and control zones of the test strip, separated by the visible barrier 120, such as tape, can be observed by the user. In certain aspects of the present invention, there may be two or more results observation windows 425, the portion of casing between the windows acting as a visible barrier 120.

In another aspect of the present invention, indicia 451 on the case 410 will indicate to the user where to apply the sample (in FIG. 4A, denoted by "S") and view the test "T" and control "C" results. It is well known by those in the art that more that one analyte may be tested on a single test strip. For example, in drug of abuse testing, often three or more different drugs are tested for on a single test strip. In this case, the indicia 415 would indicate to the user where each line will appear and what drug each test line corresponds to. For example, the indicia may read, from left to right, Amp, Barb, Coc, indicating test line locations for amphetamine, barbiturates and cocaine.

FIGS. 4B and 4C illustrate what test results might look like, in this aspect of the present invention. For example, if the test was a standard sandwich assay for HCG (i.e., pregnancy), and a positive sample was applied to the test strip, a colored line would appear at the test result zone "T" and a colored smear in the control result zone "C". The line at "T" indicates that the sample came from a pregnant donor and the line at "C" tells the user that enough time has passed, since application of the sample, to read the test results (see FIG. 4B). If, however, a negative sample was applied, no line would appear at "T" and the same color smear would appear at "C". The appearance of the smear at "C" tells the user that the test has run long enough to produce results. The user may then read the test results. The lack of a line at "T" tells the user that the sample came from a non-pregnant donor.

In additional embodiments of the present invention, the present invention may be used in conjunction with sandwich immunoassays or competitive immunoassays. Both types of assays are well established in the literature. Each type of assay has test results that are particular to the individual type of assay.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. In combination with a lateral flow analysis device of the type wherein a test strip having a sample application area, a test results zone, a control zone and optionally a reagent zone, is provided for detecting an analyte by an immunological or chemical technique, the analyte suspected of being present in a liquid sample, wherein the analyte is a drug, a hormone, an antibody, an etiological agent, a bacterium, a virus, or a portion thereof, or an antibody specific for that drug, and wherein the analyte is indicative of an etiological or disease state, the improvement comprising a first detectable and mobilizable dye indicator and a second detectable and immobilizable dye indicator located in the control zone, wherein the first detectable and mobilizable dye indicator prevents the second detectable and immobilizable dye indicator from visual detection by a user until contacted by an applied fluid sample thereby causing migration of the first detectable and mobilizable dye through said test strip by capillary flow of the applied fluid sample, the movement of said first detectable and mobilizable dye indicator being indicative of the movement of at least a portion of the fluid sample through the test result zone and optionally the completion of the assay.

2. The improvement of claim 1, wherein the downstream movement of said first detectable and mobilizable dye indicator produces an apparent color change in the control zone indicative of movement of at least a portion of the sample thorough the test result zone and optionally the completion of the assay.

3. The improvement of claim 1, wherein the test strip is bibulous.

4. The improvement of claim 1, wherein the test strip is nonbibulous.

5. An improvement for a lateral flow analytical test device for detecting an analyte suspected of being present in a sample, the improvement being a procedural control comprising:
 a) a test strip;
 b) a control zone;
 c) a test results zone, wherein the control zone is disposed downstream of the test results zone; and
 d) a control detection means for allowing a user to determine that at least a portion of a fluid sample applied to the device has migrated through said test results zone signaling completion of the assay, the control detection means comprising a first mobilizable and detectable dye reagent and a second immobilizable and detectable dye reagent,
wherein the first mobilizable and detectable dye reagent prevents the second immobilizable and detectable dye reagent from visual detection by a user until at least a portion of the fluid sample has moved through the control zone thereby causing migration of the first mobilizable and detectable dye reagent, and wherein movement of the first mobilizable and detectable dye reagent indicates that the at least a portion of the sample has moved through said test results zone signaling completion of the assay.

6. The improvement of claim 5, wherein the first mobilizable and detectable dye reagent has a first color.

7. The improvement of claim 6, wherein said color is visibly or instrumentally detectable.

8. The improvement of claim 6, wherein the second immobilizable and detectable dye reagent has a detectable color different from the first color and movement of said first mobilizable and detectable dye reagent results in a color change in the control zone.

* * * * *